United States Patent
Dong et al.

(10) Patent No.: US 10,869,615 B2
(45) Date of Patent: Dec. 22, 2020

(54) WEARABLE ELECTRONIC DEVICE AND EMOTION MONITORING METHOD

(71) Applicants: BOE TECHNOLOGY GROUP CO., LTD., Beijing (CN); BEIJING BOE OPTOELECTRONICS TECHNOLOGY CO., LTD., Beijing (CN)

(72) Inventors: Ruijun Dong, Beijing (CN); Chenru Wang, Beijing (CN); Lili Chen, Beijing (CN); Jianjie Wu, Beijing (CN)

(73) Assignees: BOE TECHNOLOGY GROUP CO., LTD., Beijing (CN); BEIJING BOE OPTOELECTRONICS TECHNOLOGY CO., LTD., Beijing (CN)

(*) Notice: Subject to any disclaimer, the term of this patent is extended or adjusted under 35 U.S.C. 154(b) by 0 days.

(21) Appl. No.: 15/548,033

(22) PCT Filed: Jan. 20, 2016

(86) PCT No.: PCT/CN2016/071469
§ 371 (c)(1),
(2) Date: Aug. 1, 2017

(87) PCT Pub. No.: WO2017/000546
PCT Pub. Date: Jan. 5, 2017

(65) Prior Publication Data
US 2018/0242887 A1   Aug. 30, 2018

(30) Foreign Application Priority Data
Jul. 1, 2015 (CN) .......................... 2015 1 0378263

(51) Int. Cl.
*A61B 5/11*   (2006.01)
*A61B 5/16*   (2006.01)
(Continued)

(52) U.S. Cl.
CPC ............... *A61B 5/11* (2013.01); *A61B 5/024* (2013.01); *A61B 5/16* (2013.01); *A61B 5/165* (2013.01); *A61B 5/486* (2013.01); *A61B 5/01* (2013.01)

(58) Field of Classification Search
None
See application file for complete search history.

(56) References Cited

U.S. PATENT DOCUMENTS 6,728,679 B1 *  4/2004  Strubbe .................. G06F 3/011
                                                                704/270.1
7,073,129 B1 *  7/2006  Robarts .................. G06Q 10/10
                                                                463/36
(Continued)

FOREIGN PATENT DOCUMENTS

CN    103040443 A    4/2013
CN    103876711 A    6/2014
(Continued)

OTHER PUBLICATIONS

First Office Action for Chinese Application No. 201510378263.0, dated Mar. 2, 2017, 11 Pages.
(Continued)

*Primary Examiner* — Carl H Layno
*Assistant Examiner* — Manolis Pahakis
(74) *Attorney, Agent, or Firm* — Brooks Kushman P.C.

(57) ABSTRACT

A wearable electronic device and an emotion monitoring method are provided. The wearable electronic device includes: a physiological data monitoring sensor configured to acquire current physiological state data of a wearer in real time; a data memory configured to pre-store physiological state data of the wearer in a preset emotional state; a first comparator configured to compare the current physiological state data acquired by the physiological data monitoring sensor with the pre-stored physiological state data, so as to
(Continued)

determine whether or not the wearer is currently in the preset emotional state, thereby to acquire a first comparison result; and an instruction generator configured to generate an emotional monitoring output instruction in accordance with the first comparison result.

11 Claims, 4 Drawing Sheets

(51) Int. Cl.
*A61B 5/024* (2006.01)
*A61B 5/00* (2006.01)
*A61B 5/01* (2006.01)

(56) References Cited

U.S. PATENT DOCUMENTS

| | | | |
|---|---|---|---|
| 8,622,901 B2* | 1/2014 | Jain | A61B 5/0022 600/300 |
| 8,718,447 B2* | 5/2014 | Yang | G06F 16/436 386/278 |
| 9,060,686 B2* | 6/2015 | Abe | A61B 5/0048 |
| 2001/0049471 A1* | 12/2001 | Suzuki | A61B 5/0002 600/300 |
| 2002/0028988 A1 | 3/2002 | Suzuki et al. | |
| 2003/0219708 A1* | 11/2003 | Janevski | H04N 21/44012 434/350 |
| 2005/0097179 A1* | 5/2005 | Orme | H04L 51/12 709/207 |
| 2008/0235284 A1* | 9/2008 | Aarts | A61B 5/0533 |
| 2009/0002178 A1* | 1/2009 | Guday | A61B 5/0002 340/573.1 |
| 2009/0013052 A1* | 1/2009 | Robarts | G06Q 10/107 709/206 |
| 2009/0128487 A1* | 5/2009 | Langereis | A61B 5/0205 345/157 |
| 2011/0263946 A1* | 10/2011 | el Kaliouby | A61B 5/1128 600/300 |
| 2012/0063654 A1* | 3/2012 | Kim | G06F 19/00 382/128 |
| 2012/0110179 A1* | 5/2012 | van Coppenolle | H04L 12/00 709/225 |
| 2012/0278413 A1* | 11/2012 | Walsh | H04L 51/14 709/206 |
| 2012/0289793 A1 | 11/2012 | Jain et al. | |
| 2012/0306643 A1* | 12/2012 | Dugan | A61B 5/02 340/539.12 |
| 2013/0007618 A1* | 1/2013 | Dodson | H04N 21/4828 715/716 |
| 2013/0080565 A1* | 3/2013 | van Coppenolle | G06Q 30/02 709/213 |
| 2013/0211277 A1* | 8/2013 | Berg | A61B 5/053 600/547 |
| 2014/0085101 A1* | 3/2014 | Rahman | A61B 5/0022 340/870.01 |
| 2014/0114899 A1* | 4/2014 | Wan | G06N 5/04 706/47 |
| 2014/0161421 A1* | 6/2014 | Shoemaker | G06T 7/0016 386/278 |
| 2014/0206946 A1* | 7/2014 | Kim | A61B 5/165 600/301 |
| 2014/0223462 A1* | 8/2014 | Aimone | H04N 21/4788 725/10 |
| 2014/0288401 A1* | 9/2014 | Ouwerkerk | A61B 5/0533 600/345 |
| 2014/0324749 A1* | 10/2014 | Peters | A63F 13/67 706/46 |
| 2015/0245777 A1* | 9/2015 | Della Torre | A61B 5/11 600/301 |
| 2015/0338917 A1* | 11/2015 | Steiner | H04L 9/3231 345/156 |
| 2016/0157735 A1* | 6/2016 | Zhang | A61B 5/02055 600/301 |
| 2018/0242887 A1* | 8/2018 | Dong | A61B 5/16 |

FOREIGN PATENT DOCUMENTS

| | | |
|---|---|---|
| CN | 104202932 A | 12/2014 |
| CN | 104434142 A | 3/2015 |
| CN | 104665930 A | 6/2015 |
| CN | 104905803 A | 9/2015 |
| CN | 204950975 U | 1/2016 |
| JP | 2001327472 A | 11/2001 |

OTHER PUBLICATIONS

Second Office Action for Chinese Application No. 201510378263.0, dated Jul. 20, 2017, 5 Pages.
International Search Report and Written Opinion for Application No. PCT/CN2016/071469, dated Mar. 31, 2016, 10 Pages.

* cited by examiner

WEARABLE ELECTRONIC DEVICE AND EMOTION MONITORING METHOD

CROSS-REFERENCE TO RELATED APPLICATION APPLICATIONS

This application is the U.S. national phase of PCT Application No. PCT/CN2016/071469 filed on Jan. 20, 2016, which claims priority to Chinese Patent Application No. 201510378263.0 filed on Jul. 1, 2015, the disclosures of which are incorporated in their entirety by reference herein.

TECHNICAL FIELD

The present disclosure relates to the field of smart terminal, in particular to a wearable electronic device and an emotion monitoring method.

BACKGROUND

In the modern society, with the living rhythm speeding up, more and more people are being under pressure, the age of people who suffer from major diseases tends to be lower, and most of the young and mid-aged people are in a sub-healthy state. Usually, people may be emotional in their daily lives, e.g., being depressed or anxious, but most of them may be unaware of and manage these emotions. As time passes, their normal lives and works may be adversely affected by these negative emotions, which have become a risk factor for their health.

Currently, parts of wearable electronic devices have a certain health monitoring function. Usually, it is able for these wearable electronic devices to acquire a healthy state of a wearer merely by monitoring physiological parameters, but it is impossible for them to monitor an emotional state of the wearer.

SUMMARY

An object of the present disclosure is to provide a wearable electronic device and an emotion monitoring method, so as to monitor an emotional state of a wearer.

In one aspect, the present disclosure provides in some embodiments a wearable electronic device, including: a physiological data monitoring sensor configured to acquire, in real time, current physiological state data of a wearer; a data memory configured to pre-store therein physiological state data of the wearer in a preset emotional state; a first comparator configured to compare the current physiological state data acquired by the physiological data monitoring sensor with the pre-stored physiological state data, so as to determine whether or not the wearer is currently in the preset emotional state, thereby to acquire a first comparison result; and an instruction generator configured to generate an emotional monitoring output instruction in accordance with the first comparison result.

In a possible embodiment of the present disclosure, the wearable electronic device further includes a motion monitoring sensor configured to determine a current motion state of the wearer. The data memory includes a storage sub-structure configured to store therein theoretical physiological state data ranges when the wearer is in a stable emotional state and in different motion states. The first comparator includes a comparison sub-structure configured to read from the storage sub-structure a theoretical physiological state data range where the wearer is in the stable physiological state and in a current motion state, and compare the theoretical physiological data range with the current physiological state data acquired by the physiological data monitoring sensor so as to acquire the first comparison result. When the current physiological state data is not within the theoretical physiological state data range where the wearer is in the stable emotional state and in the current motion state, the first comparison result indicates that the wearer is currently not in the stable emotional state.

In a possible embodiment of the present disclosure, the physiological data monitoring sensor includes a heart rate monitor configured to monitor a current heart rate of the wearer. The storage sub-structure includes a first storage sub-structure configured to store therein theoretical heart rate ranges where the wearer is in the stable emotional state and in different motion states. The comparison sub-structure includes a first comparison sub-structure configured to read from the first storage sub-structure a theoretical heart rate range where the wearer is in the stable emotional state and in the current motion state, and compare the theoretical heart rate range with the current heart rate acquired by the heart rate monitor, so as to acquire the first comparison result. When the current heart rate is not within the theoretical heart rate range where the wearer is in the stable emotional state and the current motion state, the first comparison result indicates that the wearer is currently not in the stable emotional state.

In a possible embodiment of the present disclosure, the physiological data monitoring sensor includes a body temperature monitor configured to monitor a current body temperature of the wearer. The storage sub-structure includes a second storage sub-structure configured to store therein theoretical body temperature ranges where the wearer is in the stable emotional state and in different motion states. The comparison sub-structure includes a second comparison sub-structure configured to read from the second storage sub-structure a theoretical body temperature range where the wearer is in the stable emotional state and in the current motion state, and compare the theoretical body temperature range with the current body temperature acquired by the body temperature monitor, so as to acquire the first comparison result. In the case that the current body temperature is not within the theoretical body temperature range where the wearer is in the stable emotional state and in the current motion state, the first comparison result indicates that the wearer is currently not in the stable emotional state.

In a possible embodiment of the present disclosure, the physiological data monitoring sensor includes a first humidity sensor configured to monitor current body surface humidity of the wearer. The storage sub-structure includes a third storage sub-structure configured to store therein theoretical body surface humidity ranges where the wearer is in the stable emotional state and in different motion states. The comparison sub-structure includes a third comparison sub-structure configured to read from the third storage sub-structure a theoretical body surface humidity range where the wearer is in the stable emotional state and in the current motion state, and compare the theoretical body surface humidity range with the current body surface humidity acquired by the first humidity monitor, so as to acquire the first comparison result. In the case that the current body surface humidity is not within the theoretical body surface humidity range where the wearer is in the stable emotional state and in the current motion state, the first comparison result indicates that the wearer is currently not in the stable emotional state.

In a possible embodiment of the present disclosure, the motion monitoring sensor includes an accelerometer, a gyroscope and/or a gravity sensor.

In a possible embodiment of the present disclosure, the wearable electronic device further includes a first information prompter configured to send a prompt message for prompting the wearer to improve the emotion in accordance with the emotion monitoring output instruction when the first comparison result indicates that the wearer is current not in the stable emotional state.

In a possible embodiment of the present disclosure, the wearable electronic device further includes a display screen configured to display thereon the prompt message.

In a possible embodiment of the present disclosure, the wearable electronic device further includes a tone adjustment unit configured to adjust a display color of the display screen into a warm tone in accordance with the emotion monitoring output instruction when the first comparison result indicates that the wearer is currently not in the stable emotional state.

In a possible embodiment of the present disclosure, the wearable electronic device further includes: a first device detector configured to detect a light-emitting device located within a predetermined distance from the wearer; and a first instruction transmitter configured to transmit a tone adjustment instruction to the light-emitting device detected by the first device detector in accordance with the emotion monitoring output instruction when the first comparison result indicates that the wearer is currently not in the stable emotional state, so as to enable the light-emitting device to emit light in a warm tone in accordance with the tone adjustment instruction.

In a possible embodiment of the present disclosure, the wearable electronic device further includes: a second device detector configured to detect an image outputting device within a predetermined distance from the wearer; and a second instruction transmitter configured to transmit an output filtering instruction to the image outputting device detected by second device detector in accordance with the emotion monitoring output instruction when the first comparison result indicates that the wearer is currently not in the stable emotional state, so as to enable the image outputting device to filter out texts and pictures containing predetermined information during displaying a content.

In a possible embodiment of the present disclosure, the wearable electronic device further includes: a second humidity sensor configured to detect current ambient humidity; a second comparator configured to compare the current body surface humidity acquired by the first humidity sensor and the current ambient humidity acquired by the second humidity sensor, so as determine whether or not the wearer is currently in a water-deficient state; and a second information prompter configure to send a prompt message for prompting the wearer to supplement water when the second comparator has determined that the wearer is currently in the water-deficient state.

In a possible embodiment of the present disclosure, the wearable electronic device further includes: a light beam sensor configured to detect current ambient light brightness in accordance with the emotion monitoring output instruction when the first comparison result indicates that the wearer is currently not in the stable emotional state; and a light beam processor configured to determine whether or not the current ambient light brightness is within a preset appropriate brightness range, and in the case that the current ambient light brightness is not within the preset appropriate brightness range, send a brightness adjustment instruction to the light-emitting device, so as to enable the light-emitting device to emit light at the brightness within the preset appropriate brightness range in accordance with the brightness adjustment instruction.

In a possible embodiment of the present disclosure, the wearable electronic device further includes: a first gas detector configured to detect an odor of the wearer; an odor processor configured to determine whether the odor is abnormal; and a third information prompter configured to send a prompt message for prompting the wearer to pay attention to a body abnormality when the order processor has determined that the odor is abnormal.

In a possible embodiment of the present disclosure, the wearable electronic device further includes: a second gas detection sensor configured to detect a gas in an ambient where the wearer is located; a gas processor configured to determine whether or not there is a hazardous substance in the gas; and a fourth information prompter configured to send a prompt message for prompting the wearer that the ambient is dangerous when the gas processor has determined that there is the hazardous substance in the gas.

In a possible embodiment of the present disclosure, the wearable electronic device further includes: a fifth information prompter configured to display the current motion state and the current physiological state data of the wearer in the form of texts or pictures, and prompt the wearer to determine whether or not the determination of the current motion state is correct; and a data writing unit configured to, when receiving an instruction indicating that the determination of the current motion state is correct, write the current motion state and the current physiological state data into the storage sub-structure, and update the theoretical physiological state data range where the wearer is in the stable emotional state and in the current motion state so as to enable the current physiological state data is within the theoretical physiological state data range.

In a possible embodiment of the present disclosure, the wearable electronic device further includes a data transmitter configured to transmit the different motion states and the corresponding theoretical physiological state data ranges stored in the storage sub-structure to a serving terminal so as to collect and store the different motion states and the corresponding theoretical physiological state data ranges in the serving terminal.

In a possible embodiment of the present disclosure, the wearable electronic device further includes a data receiver configured to receive from a serving terminal the physiological state data that conforms to physical characteristic information of the wearer in the preset emotional state.

In another aspect, the present disclosure provides in some embodiments an emotion monitoring method by use of a wearable electronic device, including steps of: acquiring current physiological state data of a wearer in real time; comparing the current physiological state data with pre-stored physiological state data of the wearer in a preset emotional state, so as to determine whether or not the wearer is currently in the preset emotional state, thereby to acquire a first comparison result; and generating an emotional monitoring output instruction in accordance with the first comparison result.

In a possible embodiment of the present disclosure, the emotion monitoring method further includes determining a current motion state of the wearer. The step of comparing the current physiological state data with the pre-stored physiological state data of the wearer in the preset emotional state, so as to determine whether or not the wearer is currently in the preset emotional state, thereby to acquire the first comparison result includes: acquiring, from a storage sub-structure of the wearable electronic device, a theoretical physiological state data range where the wearer is in a stable emotional state and in the current motion state, theoretical physiological data ranges where the wearer is in the stable emotional state and in different motion states being stored in the storage sub-structure; and comparing the theoretical physiological state data range where the wearer is in the stable emotional state and in the current motion state with the current physiological state data, and determining whether or not the current physiological state data is in the theoretical physiological state data range where the wearer is in the stable emotional state and in the current motion state so as to acquire the first comparison result. In the case that current physiological state data is not within the theoretical physiological state data range where the wearer is in the stable emotional state and in the current motion state, the first comparison result indicates that the wearer is currently not in the stable emotional state.

In a possible embodiment of the present disclosure, the step of acquiring the current physiological state data of the wearer in real time includes monitoring a current heart rate, a current body temperature and/or current body surface humidity of the wearer in real time.

In a possible embodiment of the present disclosure, the emotion monitoring method further includes, sending a prompt message for prompting the wearer to improve the emotion in accordance with the emotion monitoring output instruction when the first comparison result indicates that the wearer is currently not in the stable emotional state.

In a possible embodiment of the present disclosure, the emotion monitoring method further includes, adjusting a display color of a display screen of the wearable electronic device into a warm tone in accordance with the emotion monitoring output instruction when the first comparison result indicates that the wearer is currently not in the stable emotional state.

In a possible embodiment of the present disclosure, the emotion monitoring method further includes: detecting a light-emitting device within a predetermined distance from the wearer; and sending a tone adjustment instruction to the light-emitting device in accordance with the emotion monitoring output instruction when the first comparison result indicates that the wearer is currently not in the stable emotional state, so as to enable the light-emitting device to adjust the display color into a war tone in accordance with the tone adjustment instruction.

In a possible embodiment of the present disclosure, the emotion monitoring method further includes: detecting an image outputting device within a predetermined distance from the wearer; and sending an output filtering instruction to the image outputting device in accordance with the emotion monitoring output instruction when the first comparison result indicates that the wearer is currently not in the stable emotional state, so as to enable the image outputting device to filter out texts and pictures containing predetermined information during displaying a content.

According to the embodiments of the present disclosure, the wearable electronic device may monitor and acquire in real time the current physiological state data of the wearer, and compare it with the pre-stored physiological state data. As a result, it is able for the wearable electronic device to determine whether or not the current emotional state of the wearer is the preset emotional state, thereby to monitor the emotion of the wearer.

DETAILED DESCRIPTION OF THE EMBODIMENTS

In order to make the technical solutions and the advantages of the present disclosure more apparent, the present disclosure will be described hereinafter in conjunction with the drawings and embodiments.

Figure 1:
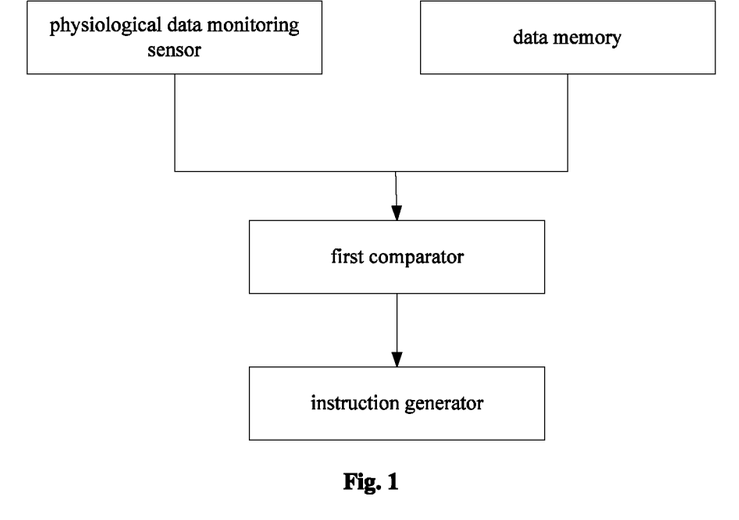
FIG. 1 is a schematic view showing a wearable electronic device according to some embodiments of the present disclosure.

As shown in FIG. 1, the present disclosure provides in some embodiments a wearable electronic device, which includes: a physiological data monitoring sensor configured to acquire, in real time, current physiological state data of a wearer; a data memory configured to pre-store therein physiological state data of the wearer in a preset emotional state; a first comparator configured to compare the current physiological state data acquired by the physiological data monitoring sensor with the pre-stored physiological state data, so as to determine whether or not the wearer is currently in the preset emotional state, thereby to acquire a first comparison result; and an instruction generator configured to generate an emotional monitoring output instruction in accordance with the first comparison result.

According to the embodiments of the present disclosure, the wearable electronic device may monitor and acquire in real time the current physiological state data of the wearer, and compare it with the pre-stored physiological state data. As a result, it is able for the wearable electronic device to determine whether or not the current emotional state of the wearer is the preset emotional state, thereby to monitor the emotion of the wearer.

In the embodiments of the present disclosure, physiological state data of the wearer in a stable emotional state may be pre-stored in the data memory. In the case that the physiological data monitoring sensor has acquired the current physiological state data, the first comparator may compare the current physiological state data of the wearer with the physiological state data of the wearer in the stable emotional state pre-stored in the data memory. In the case that the current physiological state data does not conform to the physiological state data of the wearer in the stable emotional state pre-stored in the data memory, the first comparison result indicates that the wearer is currently not in the stable emotional state, i.e., the wearer is currently in an abnormal emotional state. In the case that the current physiological state data conforms to the physiological state data of the wearer in the stable emotional state pre-stored in the data memory, the first comparison result indicates that the wearer is currently in the stable emotional state.

Of course, physiological state data of the wearer in the abnormal emotional state may also be pre-stored in the data memory. Similarly, in the case that the current physiological state data conforms to the physiological state data of the wearer in the abnormal emotional state pre-stored in the data memory, the first comparison result indicates that the wearer is currently in the abnormal emotional state. In the case that the current physiological state data does not conform to the physiological state data of the wearer in the abnormal emotional state pre-stored in the data memory, the first comparison result indicates that the wearer is currently not in the abnormal emotional state.

It should be appreciated that, the abnormal emotion of the wearer may include anger, anxiety, depression, excitement, etc. In the case that the wearer is in one of these emotions for a long time period, the body of the wearer may be adversely affected. Through the wearable electronic device in the embodiments of the present disclosure, it is able to monitor any emotional change of the wearer, thereby to prompt in real time the wearer to manage the emotion in time.

To be specific, the physiological state data of the wearer in the current emotional state may include heart rate, body temperature and/or body surface humidity. It should be appreciated that, in the case that the wearer is in the stable emotional state, the heart rate, the body temperature and/or the body surface humidity may be in a relatively stable state, i.e., the wearer may have stable physiological state data. In the case that the wearer is in the abnormal emotional state (e.g., the wearer is angry, anxious, depressed or excited), the heart rate and the body temperature may change, and meanwhile such symptoms as sweatiness may occur. Through monitoring the physiological state data, it is able to determine the emotional change of the wearer.

Figure 2:
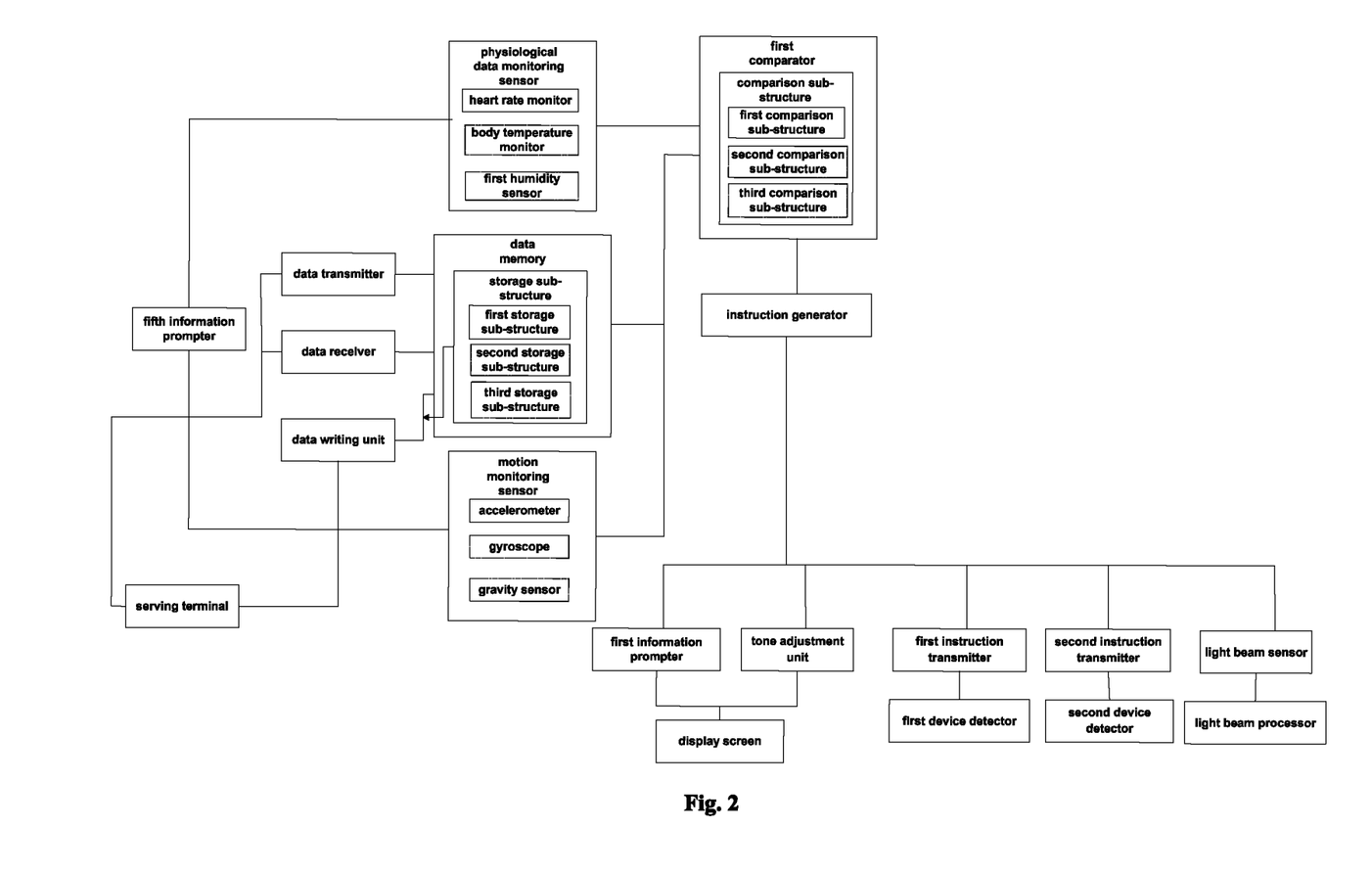
FIG. 2 is another schematic view showing the wearable electronic device according to some embodiments of the present disclosure.

As shown in FIG. 2, the wearable electronic device includes: a physiological data monitoring sensor configured to acquire, in real time, current physiological state data of a wearer; a data memory configured to pre-store therein physiological state data of the wearer in a preset emotional state; a first comparator configured to compare the current physiological state data acquired by the physiological data monitoring sensor with the pre-stored physiological state data, so as to determine whether or not the wearer is currently in the preset emotional state, thereby to acquire a first comparison result; and an instruction generator configured to generate an emotional monitoring output instruction in accordance with the first comparison result.

In a possible embodiment of the present disclosure, the wearable electronic device further includes a motion monitoring sensor configured to determine a current motion state of the wearer. The data memory includes a storage sub-structure configured to store therein theoretical physiological state data ranges in the case that the wearer is in a stable emotional state and in different motion states. The first comparator includes a comparison sub-structure configured to read from the storage sub-structure a theoretical physiological state data range where the wearer is in the stable physiological state and in a current motion state, and compare the theoretical physiological data range with the current physiological state data acquired by the physiological data monitoring sensor so as to acquire the first comparison result. In the case that current physiological state data is not within the theoretical physiological state data range where the wearer is in the stable emotional state and in the current motion state, the first comparison result indicates that the wearer is currently not in the stable emotional state.

In the embodiments of the present disclosure, different motion states of the wearer are corresponding to different physiological state data. For example, the wearer is sitting still, walking or running, the wearer's heart rate and body temperature may be different. The theoretical physiological state data ranges where the wearer is in the stable emotional state and in different motion states, e.g., heart rate ranges of the wearer in the case that the wearer is sitting still, walking and running, may be stored in the storage sub-structure. The motion monitoring sensor may determine the current motion state of the wearer, so as to determine whether or not the wearer is sitting still, walking or running. The physiological data monitoring sensor may acquire the current physiological state data of the wearer, and the comparison sub-structure may compare the current physiological state data with the theoretical physiological state data range (where the wearer is in the stale emotional state and in the current motion state) stored in the storage sub-structure. In the case that the current physiological state data is not within the theoretical physiological state data range where the wearer is in the stable emotional state and in the current motion state, the first comparison result indicates that the wearer is currently not in the stable emotional state. For example, the current motion state of the wearer is walking at a predetermined speed, and the current physiological state data acquired by the physiological data monitoring sensor is heart rate. At this time, the acquired current heart rate may be compared with a theoretical heart rate range (where the wearer is in the stable emotional state and in a walking state at the predetermined speed) stored in the storage sub-structure. In the case that the heart rate acquired in the walking state is not within the theoretical heart rate range where the wearer is in the stable emotional state and in the walking state, it is able to determine that the wearer is currently not in the stable emotional state.

To be specific, the theoretical physiological state data ranges stored in the storage sub-structure may include theoretical physiological state data ranges where the wearer is in the stable emotional state and in different motion states (e.g., a still-sitting state, walking states at different speeds, and running states at different speeds).

In addition, the motion monitoring sensor for determining the current motion state of the wearer may include an accelerometer, a gyroscope and/or a gravity sensor. Through one of, or preferably at least two of, the accelerometer, the gyroscope and the gravity sensor, it is able to accurately determine the current motion state of the wearer. It is well known in the art to apply the accelerometer, the gyroscope and/or the gravity sensor to the wearable electronic device, so as to determine the motion state of the wearer, which will thus not be particularly defined herein. Of course, in the related art, the elements capable of determining the motion state of the wearer are not limited to the above-mentioned members.

In some embodiments of the present disclosure, the physiological state data of the wearer in the current emotional state may include heart rate. In the case that the heart rate is used as the physiological state data to determine the current emotional state of the wearer, as shown in FIG. 2, in the wearable electronic device, the physiological data monitoring sensor specifically includes a heart rate monitor configured to monitor a current heart rate of the wearer. The storage sub-structure includes a first storage sub-structure configured to store therein theoretical heart rate ranges where the wearer is in the stable emotional state and in different motion states. The comparison sub-structure includes a first comparison sub-structure configured to read from the first storage sub-structure a theoretical heart rate range where the wearer is in the stable emotional state and in the current motion state, and compare the theoretical heart rate range with the current heart rate acquired by the heart rate monitor, so as to acquire the first comparison result. In the case that the current heart rate is not within the theoretical heart rate range where the wearer is in the stable emotional state and the current motion state, the first comparison result indicates that the wearer is currently not in the stable emotional state. In other words, through the heart rate monitor, the first storage sub-structure and the first comparison sub-structure, it is able to monitor the heart rate of the wearer, thereby to determine the current emotional state of the wearer.

In addition, in some embodiments of the present disclosure, the physiological state data of the wearer in the current emotional state may also include body temperature. In the case that the body temperature is used as the physiological state data to determine the current emotional state of the wearer, as shown in FIG. 2, in the wearable electronic device, the physiological data monitoring sensor includes a body temperature monitor configured to monitor a current body temperature of the wearer. The storage sub-structure includes a second storage sub-structure configured to store therein theoretical body temperature ranges where the wearer is in the stable emotional state and in different motion states. The comparison sub-structure includes a second comparison sub-structure configured to read from the second storage sub-structure a theoretical body temperature range where the wearer is in the stable emotional state and in the current motion state, and compare the theoretical body temperature range with the current body temperature acquired by the body temperature monitor, so as to acquire the first comparison result. In the case that the current body temperature is not within the theoretical body temperature range where the wearer is in the stable emotional state and in the current motion state, the first comparison result indicates that the wearer is currently not in the stable emotional state. In other words, through the body temperature monitor, the second storage sub-structure and the second comparison sub-structure, it is able to monitor the body temperature of the wearer, thereby to determine the current emotional state of the wearer.

Further, in some embodiments of the present disclosure, the physiological state data of the wearer in the current emotional state may also include body surface humidity. In the case that the body surface humidity is used as the physiological state data to determine the current emotional state of the wearer, as shown in FIG. 2, in the wearable electronic device, the physiological monitoring sensor includes a first humidity sensor configured to monitor current body surface humidity of the wearer. The storage sub-structure includes a third storage sub-structure configured to store therein theoretical body surface humidity ranges where the wearer is in the stable emotional state and in different motion states. The comparison sub-structure includes a third comparison sub-structure configured to read from the third storage sub-structure a theoretical body surface humidity range where the wearer is in the stable emotional state and in the current motion state, and compare the theoretical body surface humidity range with the current body surface humidity acquired by the first humidity monitor, so as to acquire the first comparison result. In the case that the current body surface humidity is not within the theoretical body surface humidity range where the wearer is in the stable emotional state and in the current motion state, the first comparison result indicates that the wearer is currently not in the stable emotional state.

In a possible embodiment of the present disclosure, in the case that the body surface humidity is used as the physiological state data to determine the current emotional state of the wearer, the wearable electronic device may further include an ambient temperature sensor configured to detect a current ambient temperature. The third storage sub-structure is further configured to store therein theoretical body surface humidity ranges where the wearer is in the stable emotional state, at different ambient temperatures and in different motion states. The third comparison sub-structure is further configured to compare the current body surface humidity with the theoretical body surface humidity range where the wearer is in the stable emotional state, at a current ambient temperature and in the current motion state. In the case that the current body surface humidity is not within the theoretical physiological body surface humidity range, it is able to determine that the wearer is currently not in the stable emotional state. In other words, due to different body surface humidity at different ambient temperatures and in different motion states, it is necessary to determine whether or not the current body surface humidity is within the theoretical body surface humidity range where the wearer is in the stable emotional state, at the current ambient temperature and in the current motion state, thereby to determine whether or not the wearer is currently in the stable emotional state.

In addition, the wearable electronic device may determine whether or not the wearer is currently in the stable emotional state in accordance with at least two of the heart rate, the body temperature and the body surface humidity. For example, the abnormal emotional state of the wearer may be determined on the basis of the heart rate and the body temperature, so as to ensure the accuracy of the determination result.

It should be appreciated that, on the basis of the principle of determining the emotional state of the wearer in accordance with the physiological state data and the motion state, the physiological state data of the wearer in the current emotional state may include any other parameters, apart from the heart rate, the body temperature and/or the body surface humidity.

In addition, it should be further appreciated that, the structures and the implementations of the heart rate monitor, the body temperature monitor and the first humidity sensor of the wearable electronic device are known in the art, and thus will not be particularly defined herein.

In the embodiments of the present disclosure, in the wearable electronic device for determining the emotional state of the wearer in the above-mentioned ways, the theoretical physiological state data ranges (where the wearer is in the stable emotional state and in different motion states) stored in the respective storage sub-structures may be determined in various modes. In one mode (i.e., a data collection mode), the physiological data monitoring sensor may collect the physiological state data of the wearer for a long time period, then the corresponding motion states of the wearer may be determined by the motion monitoring sensor, and then the results from the motion monitoring sensor may be confirmed by the wearer and stored. Through the data accumulation for a long time, it is able to acquire the theoretical physiological state data range where the wearer in the stable emotional state and in different motion states.

As shown in FIG. 2, the wearable electronic device may further include: a fifth information prompter configured to display the current motion state and the current physiological state data of the wearer in the form of pictures or texts, and prompt the wearer to determine whether or not the determination of the current motion state is correct; and a data writing unit configured to, in the case of receiving an instruction indicating that the determination of the current motion state is correct, write the current motion state and the current physiological state data into the storage sub-structure correspondingly, and update the theoretical physiological state data range where the wearer is in the stable emotional state and in the current motion state so as to enable the current physiological state data is within the theoretical physiological state data range.

In a possible embodiment of the present disclosure, the wearable electronic device further includes a data transmitter configured to transmit the different motion states and the corresponding theoretical physiological state data ranges stored in the storage sub-structure to a serving terminal so as to collect and store the different motion states and the corresponding theoretical physiological state data ranges in the serving terminal.

In this regard, after the removal of private information, the data including the theoretical physiological state data ranges of the wearer may be uploaded by the data transmitter to the serving terminal, so as to collect and store the data in the serving terminal.

On the basis of the data collection, the theoretical physiological state data ranges (where the wearer is in the stable emotional state and in different motion states) stored in the storage sub-structure may also be directly downloaded from a data base in the serving terminal, and then stored in the wearable electronic device. At this time, the wearable electronic device may further include a data receiver configured to receive from a serving terminal the theoretical physiological state data range that conforms to physical characteristic information of the wearer in the preset emotional state and in different motion states.

For example, in the case that the theoretical physiological state data ranges where the wearer is in the stable emotional state and in different motion states have been collected by the serving terminal, the wearable electronic device may report the body characteristic information (including age, gender, height and weight) of the wearer to the serving terminal, so as to directly download from the serving terminal the theoretical physiological state data ranges that conforms to physical characteristic information of the wearer in the stable emotional state and in different motion states.

As shown in FIG. 2, the wearable electronic device may further include a first information prompter connected to the instruction generator and configured to, receive the emotion monitoring output instruction from the instruction generator, and send a prompt message for prompting the wearer to improve the emotion in accordance with the emotion monitoring output instruction when the first comparison result indicates that the wearer is currently not in the stable emotional state. To be specific, the prompt message may be sent in a voice form.

In a possible embodiment of the present disclosure, the wearable electronic device may further include a display screen configured to display thereon the prompt message. To be specific, the prompt message may be displayed in texts or pictures.

In a possible embodiment of the present disclosure, as shown in FIG. 2, the wearable electronic device may further include a tone adjustment unit configured to, in the case that the first comparison result indicates that the wearer is currently not in the stable emotional state, adjust a display color of the display screen into a warm tone in accordance with the emotion monitoring output instruction. Through the adjustment of the display color of the display screen into the warm tone, it is able to help the wearer to adjust the emotion state into a stable and peace emotional state.

In a possible embodiment of the present disclosure, as shown in FIG. 2, the wearable electronic device may further include: a first device detector configured to detect a light-emitting device located within a predetermined distance from the wearer; and a first instruction transmitter configured to, in the case that the first comparison result indicates that the wearer is currently not in the stable emotional state, transmit a tone adjustment instruction to the light-emitting device detected by the first device detector in accordance with the emotion monitoring output instruction, so as to enable the light-emitting device to emit light in a warm tone in accordance with the tone adjustment instruction.

To be specific, the light-emitting device may be any other electronic device which is currently being used by the wearer, e.g., a computer or a mobile phone. Through the detection of the light-emitting devices within predetermined distance from the wearer by the first device detector, the wearable electronic device may communicate with the light-emitting devices in a wireless form, when the wearer is currently not in the stable emotional state, the wearable electronic device may transmit the tone adjustment instruction to the light-emitting device, so as to enable the light-emitting device to emit the light in the warm tone, thereby to help the wearer to adjust the emotion.

In a possible embodiment of the present disclosure, the wearable electronic device may further include: a light beam sensor configured to, in the case that the first comparison result indicates that the wearer is currently not in the stable emotional state, detect current ambient light brightness in accordance with the emotion monitoring output instruction; and a light beam processor configured to determine whether or not the current ambient light brightness is within a predetermined appropriate brightness range, and when the current ambient light brightness is not within the predetermined appropriate brightness range, send a brightness adjustment instruction to the light-emitting device, so as to enable the light-emitting device to emit light at the brightness within the predetermined appropriate brightness range in accordance with the brightness adjustment instruction.

In this way, it is able to adjust the light brightness of the light-emitting device (e.g., a lamp, a display screen of a computer, or a mobile phone) in the ambient where the wearer is located, so as to help the wearer to adjust the emotion.

In a possible embodiment of the present disclosure, as shown in FIG. 2, the wearable electronic device may further include: a second device detector configured to detect an image outputting device within a predetermined distance from the wearer; and a second instruction transmitter configured to, in the case that the first comparison result indicates that the wearer is currently not in the stable emotional state, transmit an output filtering instruction to the image outputting device detected by second device detector in accordance with the emotion monitoring output instruction, so as to enable the image outputting device to filter out texts and pictures containing predetermined information in the case of displaying a content.

To be specific, the image outputting device may also be any other electronic device which is currently being used by the wearer, e.g., a computer or a mobile phone. The wearable electronic device has a wireless communication function with the image outputting device, and the image outputting device may have a function of filtering out content displayed thereon in accordance with an instruction from the wearable electronic device. In the case that the wearer is currently not in the stable emotional state, the wearable electronic device may send the output filtering instruction to the detected image outputting device, so as to enable the image outputting device to filter out the texts and pictures containing negative information from the content displayed thereon in accordance with the output filtering instruction. The texts or pictures containing the negative information may be contents that may adversely affect the emotion of the wearer, e.g., violence, misanthropy or misfortune.

Through the combination of the members in FIG. 2, it is able for the wearable electronic device to determine whether or not the current emotional state of the wearer is abnormal, thereby to monitor the emotion of the wearer. In addition, it is able to further prompt the wearer to adjust the emotion in time. Further, it is able to adjust the light brightness and tone of the other light-emitting device which is currently being used by the wearer, and filter out the contents displayed on the image outputting device which is currently being used by the wearer, thereby to help the wearer to adjust the emotion.

Figure 3:
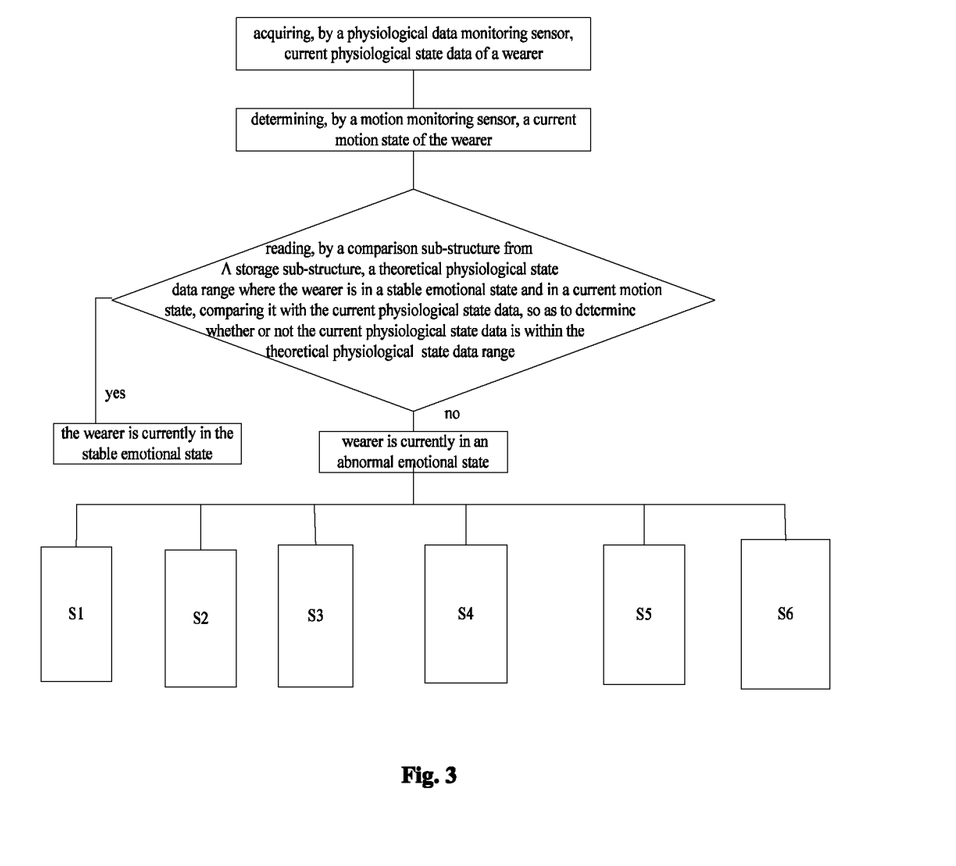
FIG. 3 is a flow chart of an emotion monitoring procedure of the wearable electronic device according to some embodiments of the present disclosure.

As shown in FIG. 3, an emotion monitoring procedure of the wearable electronic device with the above-mentioned structure will be described as follows.

The physiological data monitoring sensor may acquire the current physiological state data of the wearer. The motion monitoring sensor may determine the current motion state of the wearer. The comparison sub-structure may read from the storage sub-structure the theoretical physiological state data range where the wearer is in the stable emotional state and in the current motion state, and compare it with the current physiological state data acquired by the physiological data monitoring sensor, so as to determine whether or not the current physiological state data is within the theoretical physiological state data range. When the determination result is positive, it is able to determine that the wearer is currently in the stable emotional state, and even if there is a relatively greater difference between the current physiological state data and the previous physiological state data, it is still able to determine that the difference is caused by motion. When the determination result is negative, it is able to determine that the wearer is currently in the abnormal emotional state.

Further, when the wearer is currently in the abnormal emotional state, at least one of the following steps S1-S6 may be performed, so as to prompt the wearer or help the wearer to adjust the emotion.

S1: The first information prompter may send the prompt message for prompting the wearer to improve the emotion. S2: The display screen may display thereon the prompt message. S3: The tone adjustment unit may adjust the display color of the display screen into the warm tone. S4: The first instruction transmitter may transmit the tone adjustment instruction to the light-emitting device detected by the first device detector, so as to enable the light-emitting device to emit light in the warm tone in accordance with the tone adjustment instruction. S5: The light beam processor may determine whether or not the ambient light brightness is within the predetermined appropriate brightness range, and when a determination result is negative, send the brightness adjustment instruction to the light-emitting device, so as to enable the light-emitting device to adjust the brightness to be within the predetermined appropriate brightness range in accordance with the brightness adjustment instruction. S6: The second instruction transmitter may transmit the output filtering instruction to the image outputting device detected by the second device detector, so as to enable the image outputting device to filter out the texts and pictures containing the predetermined information.

In a possible embodiment of the present disclosure, apart from the functions of determining whether or not the current emotional state of the wearer is abnormal and sending the emotion monitoring output instruction to help the wearer to adjust the emotion, the wearable electronic device may have the other functions through the following members.

Function 1: prompting the wearer in a water-deficient state to supplement water.

To be specific, the wearable electronic device may include: a second humidity sensor configured to detect current ambient humidity; a second comparator configured to compare the current body surface humidity acquired by the first humidity sensor and the current ambient humidity acquired by the second humidity sensor, so as determine whether or not the wearer is currently in a water-deficient state; and a second information prompter configure to, in the case that the second comparator has determined that the wearer is currently in the water-deficient state, send a prompt message for prompting the wearer to supplement water.

Function 2: detecting a body state in accordance with an odor from the wearer.

To be specific, the wearable electronic device may further include: a first gas detector configured to detect an odor of the wearer; an odor processor configured to determine whether the odor is abnormal; and a third information prompter configured to, in the case that the order processor has determined that the odor is abnormal, send a prompt message for prompting the wearer to pay attention to a body abnormality.

Function 3: detecting a hazardous substance in an ambient gas.

To be specific, the wearable electronic device may further include: a second gas detection sensor configured to detect a gas in an ambient where the wearer is located; a gas processor configured to determine whether or not there is a hazardous substance in the gas; and a fourth information prompter configured to, in the case that the gas processor has determined that there is the hazardous substance in the gas, send a prompt message for prompting the wearer that the ambient is dangerous.

Of course, apart from the above-mentioned functions, the wearable electronic device may further have any other functions, e.g., an eyestrain prompting function, which will not be particularly defined herein.

Figure 4A:
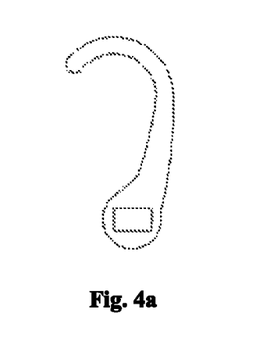
FIGS. 4a to 4c are schematic views showing an appearance of the wearable electronic device according to some embodiments of the present disclosure.
Figure 4B:
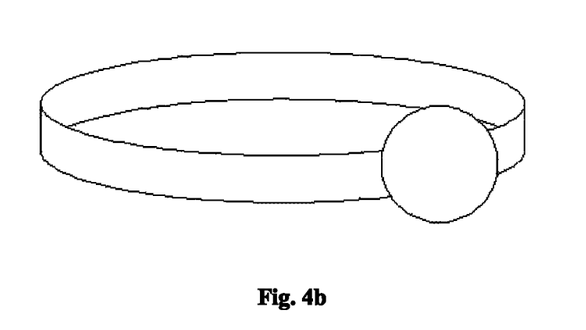
Figure 4C:
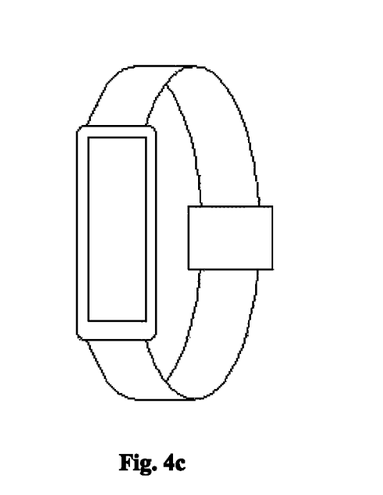

FIGS. 4a to 4c show appearances of the wearable electronic device. In the case that the wearable electronic device has a hoop as shown in FIG. 4a, it may be directly attached onto an ear of the wearer; in the case that it has a circular structure with a large diameter as shown in FIG. 4b (e.g., a collar), it may be directly sleeved onto the neck of the wearer; and in the case that it has a circular structure with a small diameter as shown in FIG. 4c (e.g., a bracelet), it may be directly sleeved onto a wrist of the wearer.

The present disclosure further provides in some embodiments an emotion monitoring method by use of a wearable electronic device, which includes steps of: acquiring, in real time, current physiological state data of a wearer; comparing the current physiological state data with pre-stored physiological state data of the wearer in a preset emotional state, so as to determine whether or not the wearer is currently in the preset emotional state, thereby to acquire a first comparison result; and generating an emotional monitoring output instruction in accordance with the first comparison result.

In a possible embodiment of the present disclosure, the emotion monitoring method further includes determining a current motion state of the wearer. The step of comparing the current physiological state data with the pre-stored physiological state data of the wearer in the preset emotional state, so as to determine whether or not the wearer is currently in the preset emotional state, thereby to acquire the first comparison result includes: acquiring, from a storage sub-structure, a theoretical physiological state data range where the wearer is in a stable emotional state and in the current motion state, theoretical physiological data ranges where the wearer is in the stable emotional state and in different motion states being stored in the storage sub-structure; and comparing the theoretical physiological state data where the wearer is in the stable emotional state and in the current motion state with the current physiological state data, and determining whether or not the current physiological state data is in the theoretical physiological state data where the wearer is in the stable emotional state and in the current motion state so as to acquire the first comparison result. In the case that current physiological state data is not within the theoretical physiological state data range where the wearer is in the stable emotional state and in the current motion state, the first comparison result indicates that the wearer is currently not in the stable emotional state.

In a possible embodiment of the present disclosure, the step of acquiring, in real time, the current physiological state data of the wearer includes monitoring, in real time, a current heart rate, a current body temperature and/or current body surface humidity of the wearer.

In a possible embodiment of the present disclosure, the emotion monitoring method further includes, when the first comparison result indicates that the wearer is currently not in the stable emotional state, sending a prompt message for prompting the wearer to improve the emotion in accordance with the emotion monitoring output instruction.

In a possible embodiment of the present disclosure, the emotion monitoring method further includes, when the first comparison result indicates that the wearer is currently not in the stable emotional state, adjusting a display color of a display screen of the wearable electronic device into a warm tone in accordance with the emotion monitoring output instruction.

In a possible embodiment of the present disclosure, the emotion monitoring method further includes: detecting a light-emitting device within a predetermined distance from the wearer; and when the first comparison result indicates that the wearer is currently not in the stable emotional state, sending a tone adjustment instruction to the light-emitting device in accordance with the emotion monitoring output instruction, so as to enable the light-emitting device to adjust the display color into a war tone in accordance with the tone adjustment instruction.

In a possible embodiment of the present disclosure, the emotion monitoring method further includes: detecting an image outputting device within a predetermined distance from the wearer; and when the first comparison result indicates that the wearer is currently not in the stable emotional state, sending an output filtering instruction to the image outputting device in accordance with the emotion monitoring output instruction, so as to enable the image outputting device to filter out texts and pictures containing predetermined information in the case of displaying a content.

According to the wearable electronic device and the emotion monitoring method in the embodiments of the present disclosure, the current physiological state data of the wearer may be monitored and acquired in real time, and then it may be compared with the pre-stored physiological state data. As a result, it is able to determine whether or not the current emotional state of the wearer is the preset emotional state, thereby to monitor the emotion of the wearer.

The above are merely the preferred embodiments of the present disclosure. Obviously, a person skilled in the art may make further modifications and improvements without departing from the spirit of the present disclosure, and these modifications and improvements shall also fall within the scope of the present disclosure.

What is claimed is:

1. A wearable electronic device, comprising:
   a physiological data monitoring sensor configured to acquire current physiological state data of a wearer in real time;
   a data memory having stored thereon physiological state data of the wearer in a preset emotional state, wherein the preset emotional state is a stable emotional state where the physiological state data of the wearer is within a normal physiological state data range;
   a processor configured to:
      compare the current physiological state data acquired by the physiological data monitoring sensor with the physiological state data of the wearer in the preset emotional state, to determine whether or not the wearer is currently in the preset emotional state, thereby to acquire a first comparison result;
      generate an emotion monitoring output instruction based on the first comparison result;
      detect an image outputting device within a predetermined distance from the wearer and separated from the wearable electronic device; and
      transmit based on the emotion monitoring output instruction when the first comparison result indicates that the wearer is currently not in the preset emotional state, an output filtering instruction to the image outputting device detected by the processor, wherein the image outputting device filters out texts and pictures containing predetermined emotionally adverse information during displaying a content, based on the output filtering instruction; and
   wherein the processor is further configured to adjust a display color of the image outputting device into a warm tone based on the emotion monitoring output instruction when the first comparison result indicates that the wearer is currently not in the preset emotional state.

2. The wearable electronic device according to claim 1, further comprising:
   a light beam sensor configured to detect current ambient light brightness based on the emotion monitoring output instruction when the first comparison result indicates that the wearer is currently not in the preset emotional state; and
   a light beam processor configured to determine whether or not the current ambient light brightness is within a preset appropriate brightness range, and when the current ambient light brightness is not within the preset appropriate brightness range, send a brightness adjustment instruction to the light-emitting device, so as to enable the light-emitting device to emit light at the brightness within the preset appropriate brightness range based on the brightness adjustment instruction.

3. The wearable electronic device according to claim 1, further comprising:
   a first gas detector configured to detect an odor of the wearer;
   an odor processor configured to determine whether the odor is abnormal; and
   an odor information prompter configured to send a prompt message for prompting the wearer to pay attention to a body abnormality when the odor processor has determined that the odor is abnormal.

4. The wearable electronic device according to claim 1, further comprising:
- a second gas detection sensor configured to detect a gas in an ambient environment where the wearer is located;
- a gas processor configured to determine whether or not there is a hazardous substance in the gas; and
- a gas information prompter configured to send a prompt message for prompting the wearer that the ambient is dangerous when the gas processor has determined that there is the hazardous substance in the gas.

5. The wearable electronic device according to claim 1, further comprising a motion monitoring sensor configured to determine a current motion state of the wearer, wherein
- the data memory comprises a storage sub-structure configured to store theoretical physiological state data ranges when the wearer is in the preset emotional state and in different motion states;
- the processor is further configured to read from the storage sub-structure a theoretical physiological state data range where the wearer is in a first physiological state and in the current motion state, and compare the theoretical physiological data range with the current physiological state data acquired by the physiological data monitoring sensor so as to acquire the first comparison result; and
- when the current physiological state data is not within the theoretical physiological state data range where the wearer is in the preset emotional state and in the current motion state, the first comparison result indicates that the wearer is currently not in the preset emotional state.

6. The wearable electronic device according to claim 5, wherein the physiological data monitoring sensor comprises a heart rate monitor configured to monitor a current heart rate of the wearer;
- the storage sub-structure comprises a first storage sub-structure configured to store theoretical heart rate ranges where the wearer is in the preset emotional state and in different motion states;
- the processor is further configured to read from the first storage sub-structure a theoretical heart rate range where the wearer is in the preset emotional state and in the current motion state, and compare the theoretical heart rate range with the current heart rate acquired by the heart rate monitor, to acquire the first comparison result; and
- when the current heart rate is not within the theoretical heart rate range where the wearer is in the preset emotional state and the current motion state, the first comparison result indicates that the wearer is currently not in the preset emotional state.

7. The wearable electronic device according to claim 5, wherein the physiological data monitoring sensor comprises a body temperature monitor configured to monitor a current body temperature of the wearer;
- the storage sub-structure comprises a second storage sub-structure configured to store theoretical body temperature ranges where the wearer is in the preset emotional state and in different motion states;
- the processor is further configured to read from the second storage sub-structure a theoretical body temperature range where the wearer is in the preset emotional state and in the current motion state, and compare the theoretical body temperature range with the current body temperature acquired by the body temperature monitor, to acquire the first comparison result; and
- when the current body temperature is not within the theoretical body temperature range where the wearer is in the preset emotional state and in the current motion state, the first comparison result indicates that the wearer is currently not in the preset emotional state.

8. The wearable electronic device according to claim 5, wherein the physiological data monitoring sensor comprises a first humidity sensor configured to monitor current body surface humidity of the wearer;
- the storage sub-structure comprises a third storage sub-structure configured to store theoretical body surface humidity ranges where the wearer is in the preset emotional state and in different motion states;
- the processor is further configured to read from the third storage sub-structure a theoretical body surface humidity range where the wearer is in the preset emotional state and in the current motion state, and compare the theoretical body surface humidity range with the current body surface humidity acquired by the first humidity monitor, to acquire the first comparison result; and
- when the current body surface humidity is not within the theoretical body surface humidity range where the wearer is in the preset emotional state and in the current motion state, the first comparison result indicates that the wearer is currently not in the preset emotional state.

9. The wearable electronic device according to claim 8, further comprising:
- a second humidity sensor configured to detect current ambient humidity;
- wherein the processor is further configured to compare the current body surface humidity acquired by the first humidity sensor and the current ambient humidity acquired by the second humidity sensor, to determine whether or not the wearer is currently in a water-deficient state; and
- send a prompt message for prompting the wearer to supplement water when the processor has determined that the wearer is currently in the water-deficient state.

10. The wearable electronic device according to claim 5, wherein the processor is further configured to:
- display the current motion state and the current physiological state data of the wearer in the form of pictures or texts, and prompt the wearer to determine whether or not the determination of the current motion state is correct; and
- when receiving an instruction indicating that the determination of the current motion state is correct, write the current motion state and the current physiological state data into the storage sub-structure, and update the theoretical physiological state data range where the wearer is in the preset emotional state and in the current motion state so as to enable the current physiological state data is within the theoretical physiological state data range.

11. The wearable electronic device according to claim 1, wherein the processor is further configured to send a prompt message for prompting the wearer to improve the emotion based on the emotion monitoring output instruction when the first comparison result indicates that the wearer is currently not in the preset emotional state.

* * * * *